(12) United States Patent
Bergfjord

(10) Patent No.: US 8,904,582 B2
(45) Date of Patent: Dec. 9, 2014

(54) PATIENT SUPPORT SYSTEM

(75) Inventor: Per Harald Bergfjord, East Grinstead (GB)

(73) Assignee: Elekta AB, Stockholm (SE)

( * ) Notice: Subject to any disclaimer, the term of this patent is extended or adjusted under 35 U.S.C. 154(b) by 312 days.

(21) Appl. No.: 13/453,532

(22) Filed: Apr. 23, 2012

(65) Prior Publication Data
US 2013/0276233 A1 Oct. 24, 2013

(51) Int. Cl.
A61B 6/04 (2006.01)

(52) U.S. Cl.
USPC ............................................ 5/601; 378/209

(58) Field of Classification Search
CPC ................................. A61B 6/047; A61G 13/06
USPC ................. 5/600, 601, 611; 378/209; 52/36.4
See application file for complete search history.

(56) References Cited

U.S. PATENT DOCUMENTS

| 4,340,012 A * | 7/1982 | Gustafson | 119/723 |
| 4,657,235 A * | 4/1987 | Schar | 5/611 |
| 4,885,998 A * | 12/1989 | Span et al. | 108/139 |
| 5,953,776 A * | 9/1999 | Sanders et al. | 5/611 |
| 6,502,261 B1 | 1/2003 | Harwood | |
| 7,008,105 B2 * | 3/2006 | Amann et al. | 378/209 |
| 7,543,989 B2 * | 6/2009 | Hoth et al. | 378/209 |
| 7,581,264 B2 * | 9/2009 | Mangiardi | 5/611 |
| 2007/0217575 A1 * | 9/2007 | Kaiser et al. | 378/209 |

* cited by examiner

Primary Examiner — Michael Trettel
(74) Attorney, Agent, or Firm — Sean D. Detweiler, Esq.; Morse, Barnes-Brown & Pendleton, P.C.

(57) ABSTRACT

A patient support system includes a floor cavity in the floor of a treatment room; a patient support device comprising a treatment table; a base; a first movement mechanism on which the treatment table is mounted; a second movement mechanism mounted on the base and attached to the first movement mechanism, wherein the first and second movement mechanisms are moveable independently of each other; the first movement mechanism is configured to raise and lower the treatment table and the second movement mechanism is configured to raise and lower the first movement mechanism such that in a lowered position the second movement mechanism is contained within the floor cavity.

18 Claims, 4 Drawing Sheets

PATIENT SUPPORT SYSTEM

FIELD OF THE INVENTION

The present invention relates to improvements to a patient support system (PSS) used with a Linear Accelerator (LINAC) for radiotherapy (also known as radiation therapy or radiation oncology).

BACKGROUND OF THE INVENTION

A key factor in achieving accurate delivery of radiation therapy is patient positioning. It is important that patient positioning can be carefully controlled to accurately locate the target volume to be irradiated and avoid irradiation of surrounding healthy tissue. Existing patient support systems allow for movement of the patient in all six degrees of freedom. For example, the applicant's Precise™ treatment table allows for vertical, horizontal, longitudinal and lateral table movement and both column and isocentric rotation.

In addition to accurate patient positioning it is important to allow ease of access to the treatment table/couch for the patient. Patient support systems used with LINACs need to be positioned at a suitably low height (less than 600 mm) to enable patients to easily mount and dismount the treatment couch. It is also important that the PSS is moveable to a height in the region of 1700 mm above floor level to provide for a full range of treatment with unrestricted access to a wide range of LINAC positions. For example, it may be necessary to allow access beneath the couch and treatment at extended distances.

Existing PSS devices have achieved the required range of movement by providing a compact support system in combination with a long reaching lifting mechanism. Such a device is disclosed in the applicant's earlier U.S. Pat. No. 6,502,261 (the content of which is incorporated herein by reference in its entirety). It is also known for the PSS device to be supported in a cavity or well in the floor of the treatment room. For example, a load bearing element in a well of the treatment room floor is used to mount a lifting column, which adjusts the height of a treatment couch.

It is also common for the LINAC and PSS to be used in addition to a further patient positioning system. For example, the applicant's HexaPOD™ robotic patient positioning platform, which improves the accuracy of patent positioning by highlighting and correcting for any positional discrepancies. The use of an additional patient positioning system increases the minimum height at which the patient can be positioned. This can make it more difficult for a patient to mount and dismount the treatment couch.

SUMMARY

The present invention sets out to provide an improved patient support system which alleviates the problems described above by providing a patient support system with an "ultra-low" minimum height.

In a first aspect, the invention provides a patient support system comprising a floor cavity in the floor of a treatment room; a patient support device comprising a treatment table; a base; a first movement mechanism on which the treatment table is mounted; a second movement mechanism mounted on the base and attached to the first movement mechanism, wherein the first and second movement mechanisms are moveable independently of each other; the first movement mechanism is configured to raise and lower the treatment table and the second movement mechanism is configured to raise and lower the first movement mechanism such that in a lowered position the second movement mechanism is contained within the floor cavity.

Preferably, the patient support system is configured such that in a lowered position both the first and the second movement mechanism are contained within the floor cavity.

The patient support device and system of the present invention retains all of the functionality of existing PSS devices, whereby a patient can be accurately positioned for treatment across a full range of treatment distances, but in addition allows for a patient to safely and conveniently mount and dismount the treatment table.

Preferably, the patient support system of the present invention is configured to allow the treatment table to extend no more than about 700 mm above the rim of the floor cavity in a lowered position.

More preferably, the patient support system is configured to allow the treatment table to extend about 450 mm above the rim of the floor cavity in a lowered position.

Within this specification, the term "about" is interpreted to mean optionally ±20%, preferably optionally ±10%, more preferably optionally ±5%.

Preferably, the patient support system further comprises a moveable false floor, wherein the false floor is moveable across at least part of the opening of the floor cavity.

Optionally, the false floor is hydraulically or pneumatically powered.

Preferably, the false floor is resiliently biased.

More preferably, the false floor is slideable in a direction co-planar with the floor of the treatment room.

A false floor allows the opening of the floor cavity to be at least partially covered when the PSS is in a treatment position. This prevents anything falling into the floor cavity when treatment is being carried out and also stops the risk of anyone tripping on the rim of the exposed floor cavity.

Preferably, the patient support system comprises a rectangular floor cavity in the floor of the treatment room having a depth of about 220 to 235 mm, a length of about 1530 mm and a width of about 1400 mm.

More preferably, the patient support system comprises a rectangular floor cavity in the floor of the treatment room having a depth of about 220 to 235 mm, a length of about 530 to 1030 mm and a width of about 140 mm wherein the width of the floor cavity narrows to a width of about 600 mm.

It is envisaged that the ultra-low height of the PSS of the present invention can be achieved by providing a floor cavity sufficient to house only the second movement mechanism. If the width of the floor cavity is greater than that of the second movement mechanism, the floor cavity can also house the workings of the moveable false floor.

In a second aspect, the present invention provides a patient support device comprising a treatment table; a base; a first movement mechanism on which the treatment table is mounted; a second movement mechanism mounted on the base and attached to the first movement mechanism, wherein the first and second movement mechanisms are moveable independently of each other, the first movement mechanism is configured to adjust the height of the treatment table and the second movement mechanism is configured to adjust the height of the first movement mechanism.

For the purposes of clarity and a concise description, features are described herein as part of the same or separate embodiments; however it will be appreciated that the scope of the invention may include embodiments having combinations of all or some of the features described.

BRIEF DESCRIPTION OF THE FIGURES

These and other characteristics of the present invention will be more fully understood by reference to the following detailed description in conjunction with the attached drawings, in which.

DETAILED DESCRIPTION

Figure 1:
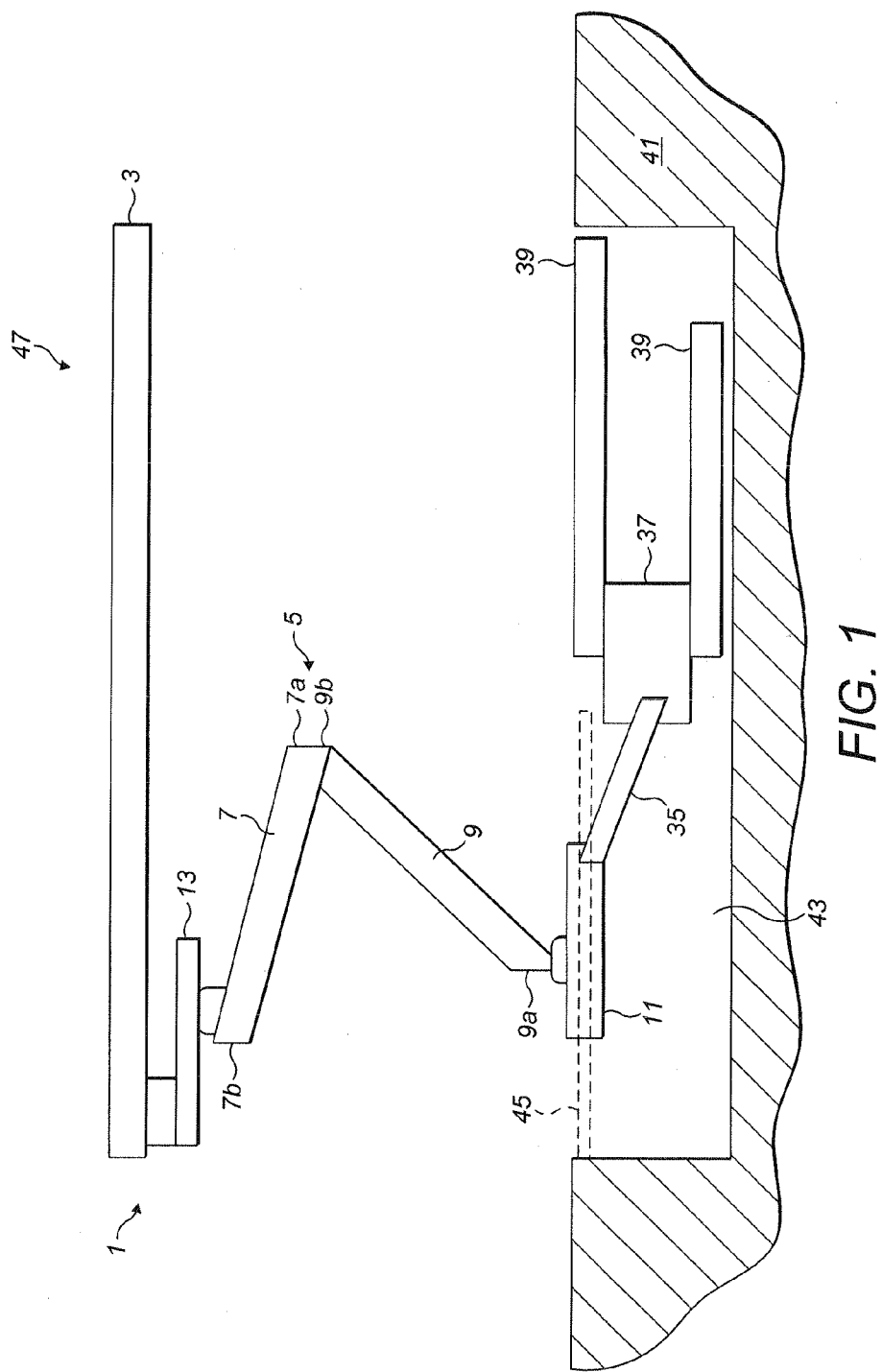
FIG. 1 is a schematic view of a patient support system constructed in accordance with an example embodiment the present invention, in a "treatment position"

FIGS. 1 through 4, wherein like parts are designated by like reference numerals throughout, illustrate example embodiments of a patient support device and system according to the present invention. Although the present invention will be described with reference to the example embodiments illustrated in the figures, it should be understood that many alternative forms can embody the present invention. One of skill in the art will additionally appreciate different ways to alter the parameters of the embodiments disclosed, such as the size, shape, or type of elements or materials, in a manner still in keeping with the spirit and scope of the present invention.

Referring to FIG. 1, an example embodiment of a patient support system (PSS) 1 is depicted. In the example embodiment of FIG. 1, the PSS 1 comprises a generally horizontal treatment table 3, to support a patient during treatment. The treatment table 3 is coupled to an upstanding support with an articulated lever arrangement, referred to as the first parallel arm mechanism 5. The first parallel arm mechanism 5 allows for a wide range of movement without increased force on the actuator of the PSS 1. The first parallel arm mechanism 5 comprises an upper arm 7 and a lower arm 9. The lower arm 9 is connected at one end 9a to a base member 11 and connected at its other end 9b to one end 7a of the upper arm 7. The other end 7b of the upper arm 7 is connected to the support member 13 on which the treatment table 3 is mounted. The treatment table 3 has a cantilever section extending beyond the support member 13 and is rotatable about the support member 13.

Figure 2:
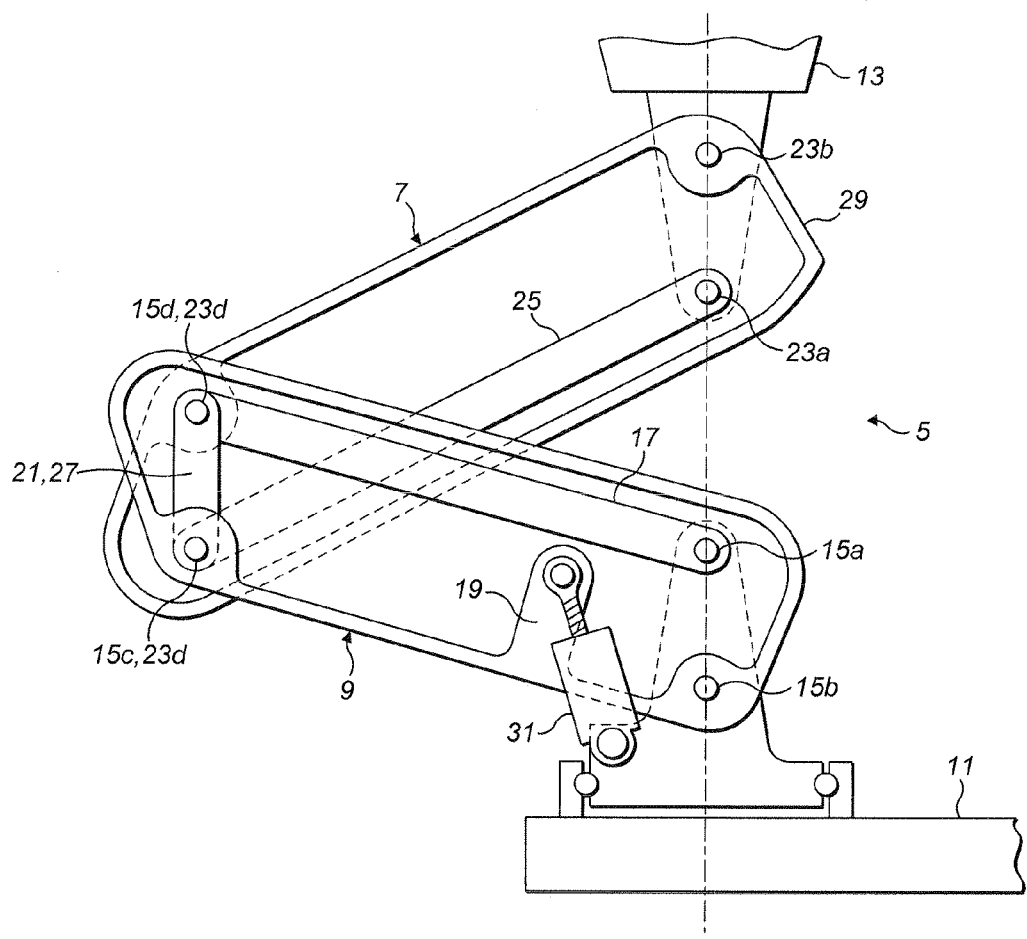
FIG. 2 is a side view of the first parallel arm mechanism of the patient support system shown in FIG. 1, in accordance with example aspects of the present invention.

Referring to FIG. 2, the first parallel arm mechanism 5 of the PSS 1 is shown from a side view. The first parallel arm mechanism 5, comprising upper and lower arms 7, 9, will now be described in more detail. Each arm 7, 9 comprises four pivot points 15a-d, 23a-d and linkages 17, 21 connecting the pivot points 15 a-d, 23a-d so as to define a parallelogram. The base member 11 of the lower arm 9 defines a first side of a parallelogram between the two pivot points 15a, 15b. A lower arm linkage 17 is pivotally connected at pivot point 15a and a lower arm outer casing 19 is pivotally connected to the pivot point 15b. The outer casing 19 is coupled to a second lower arm linkage 21 at pivot point 15c. The two linkages 17, 21 are coupled together at pivot point 15d. The four pivot points 15, 15b, 15c, 15d of the lower arm 9 define the corners of a parallelogram, with the four sides of the parallelogram effectively defined by the linkages 17, 21, the lower arm casing 19 and the base member 11. The orientation of the base member 11 is constant with respect to the support member 13 to which the treatment table 3 is attached. The base member 11 is fixed such that the orientation between the pivot points 15a, 15b is constant with respect to the base member 11.

In the example embodiment of FIGS. 1 and 2, the upper arm 7 comprises a similar arrangement whereby a parallelogram is defined by the four pivot points 23a to 23d. As for the lower arm 9, two of the sides of the parallelogram are effectively defined by upper arm linkages 25, 27 with the two other sides being defined by upper arm casing 29 and the support member 13. The upper arm linkage 27 corresponds to and has the same orientation as the lower arm linkage 21. The support member 13 has the same orientation as the base member 11. The upper and lower arms 7, 9 are coupled together side by side to allow pivoting movement between the arms 7, 9. The lower arm 9 is pivoted about the pivot point 15b by a motor actuator 31 mounted on the base member 11. The motor actuator 31 comprises a piston cylinder arrangement which is controlled to extend and retract in order to vary the angle between the base member 11 and the lower arm 9.

As shown in FIG. 2, when the parallelograms defined by the upper and lower arms 7, 9 are identical, the angular relationship between the arms 7, 9 has the effect of aligning the base member 11 with the support member 13. The motor actuator 31 is powered to lift the support member 13, and so the treatment table 3, by increasing the angle between the base member 11 and the lower arm 9. The arrangement of the first parallel arm mechanism 5 moves the support member 13 in a vertical linear direction. The treatment table 3 is also rotatably mounted on the support member 13 to rotate the treatment table 3 about the vertical axis.

In the example embodiment of FIGS. 1 and 2, the base member 11 of the first parallel arm mechanism 5 is connected to a second parallel arm mechanism 35. The second parallel arm mechanism 35 is mounted on a second base member 37, which is attached to mounting members 39. As shown, the mounting members 39 are fixed within a floor cavity 43 in the concrete floor of a treatment room 47. The mounting members 39 of the second base member 37 are bolted to the floor of the floor cavity 43, which can require, e.g., a minimum depth of about 220 mm below the floor of the floor cavity 43 to securely fix the patient support system 1 in place and safely support the patient support system's weight (e.g., of around 870 kg).

Figure 3A:
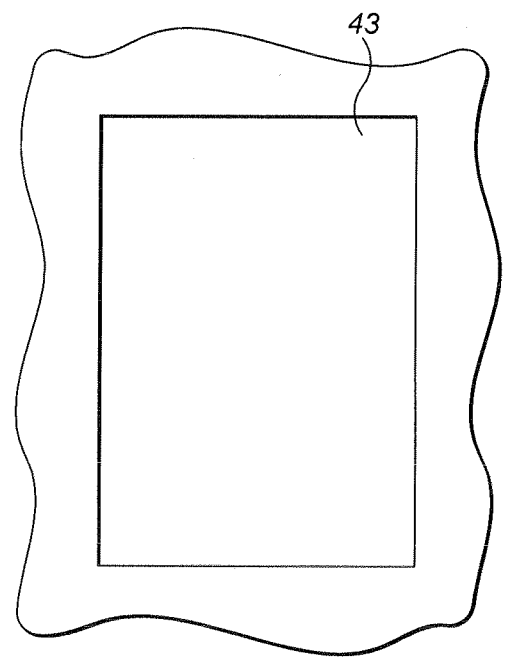
FIG. 3A is a plan view from above of the floor cavity of the patient support system shown in FIG. 1, in accordance with example aspects of the present invention.

Referring to FIG. 3A, in a first example embodiment of the present invention, the floor cavity 43 is rectangular with a depth of about 220 to 235 mm, a length of about 1530 mm and a width of about 1400 mm.

Figure 3B:
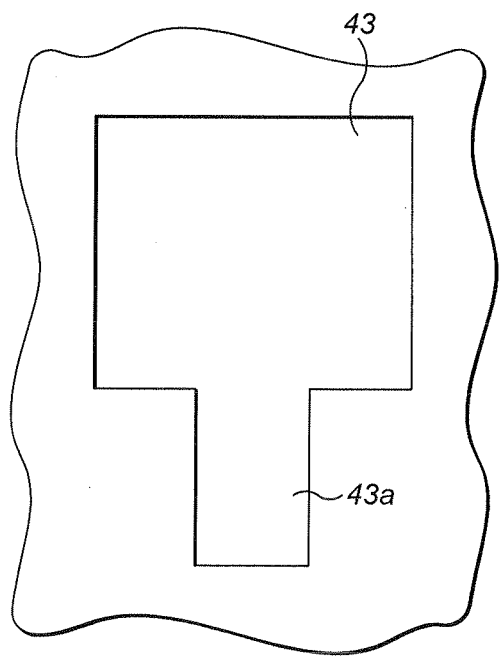
FIG. 3B is a plan view from above of the floor cavity of a patient support system in accordance to an alternative example embodiment of the present invention.

In a second example embodiment of the present invention, shown in FIG. 3B, the floor cavity 43 comprises a rectangular cavity with a depth of about 220 mm to 235 mm, a length of about 530 mm to 1030 mm and a width of about 140 mm, which narrows to a rectangular extension 43a to the floor cavity 43, with a length of about 500 mm to 1000 mm and a width of about 600 mm.

The values and dimensions provided herein are illustrative and in no way limiting of the present invention. Upon reading the present specification, one of skill in the art will appreciate a wide variety of other depths, dimensions, and the like that can be used to implement the PSS 1. All such alternatives and modifications are contemplated within the scope of the present invention. Any suitable dimensions and values can be used to implement the PSS 1.

In each of the example embodiments shown in FIGS. 3A and 3B, the floor cavity 43 houses the second parallel arm mechanism 35, the second base member 37 and the mounting members 39 below ground level within the floor cavity 43 of the treatment room 47. A minimum depth (e.g., of about 220 mm below the base of the floor cavity 43) can be implemented to safely secure the fixings of the second parallel arm mechanism 35. The floor cavity 43 also houses the first parallel arm mechanism 5 when the patient support system 1 is in a "set-up" position, as shown in FIG. 4.

Referring again to FIG. 1, a false floor 45 is moveable part-way across the floor cavity to conceal the floor cavity 43 from the treatment room 47. It is envisaged that the false floor 45 can be a sliding door co-planar with the floor of the treatment room 47. Alternatively, the false floor 45 is hydraulically or pneumatically powered; or resiliently-biased by springs to move vertically from the base of the floor cavity 43 to the floor level of the treatment room 47. In all example embodiments described herein, the false floor 45 is moveable between a "set-up" position, exposing substantially the entire opening of the floor cavity 43, to a "treatment" position wherein at least part of the floor cavity 43 is concealed by the false floor 45. In the "treatment" position, with the floor cavity 43 concealed, the false floor 45 prevents anything falling into the floor cavity 43.

Figure 4:
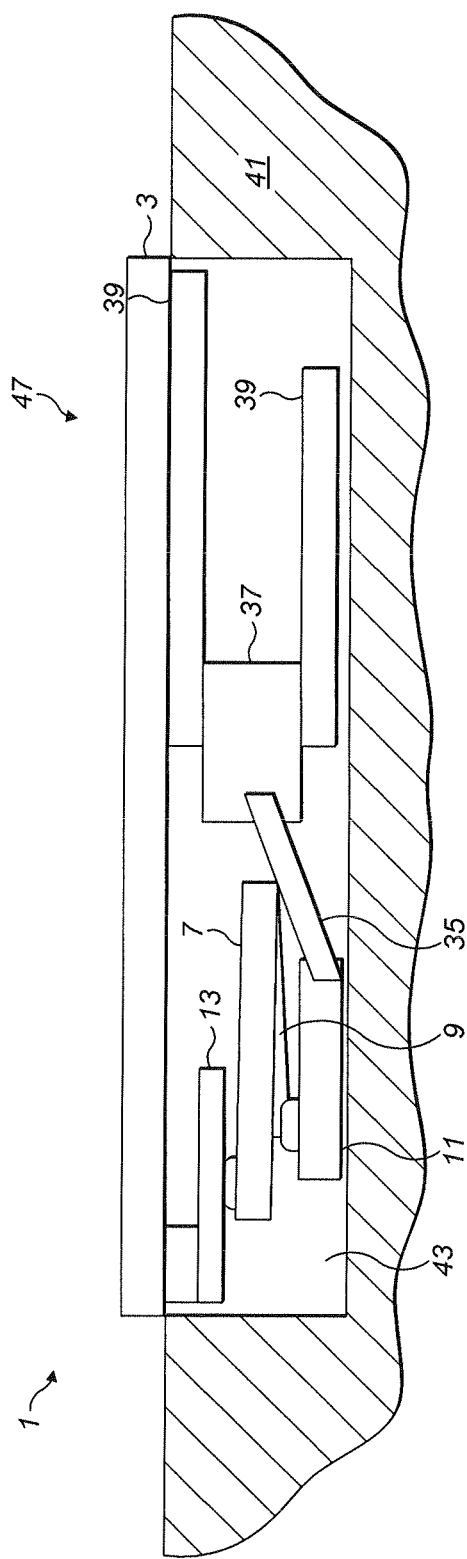
FIG. 4 is a schematic view of a patient support system constructed in accordance with an example embodiment of the present invention, in a "set-up" position.

Referring to FIG. 4, prior to treatment the false floor 45 is retracted to a "set-up" position exposing the entire opening of the floor cavity 43. The second parallel arm mechanism 35 is positioned below floor level within the floor cavity 43. The patient support system 1, including the first parallel arm mechanism 5 and the treatment table 3, are also lowered into the floor cavity 43. This lowers the treatment table 3 to its minimum height of 450 mm above the floor level of the treatment room 47. If an additional patient positioning platform is used with the treatment table 3, the treatment table 3 is lowered to a minimum height of 650 mm above the floor level of the treatment room. This allows a patient to mount the treatment table 3.

In the "set-up" position, both the first and second parallel arm mechanisms 5, 35 are contained within the floor cavity 43. With the patient mounted onto the treatment table 3, the second parallel arm mechanism 35 is used to raise the patient support system 1, including the base member 11 and the first parallel arm mechanism 5 out of the floor cavity 43 to above floor level. As shown in FIG. 1, in a "treatment" position, the false floor 45 is moved to conceal the exposed part of the floor cavity 43. It is envisaged that the false floor 45 is moved adjacent to the mounting 39 of the second parallel arm mechanism 39 so that substantially the entire opening of the floor cavity 43 is concealed.

Referring to the embodiment shown in FIG. 3B, the floor cavity 43, over which the false floor 45 moves, is only provided in the region around the central position of the patient support system 1. In the "set-up" position the patient support system 1 and the treatment table 3 are rotated to a central position with respect to the treatment table's range of rotational movement. This aligns the patient support system 1 and the treatment table 3 with the floor cavity 43 so that the first and second parallel arm mechanisms 5, 35 can be lowered and "sink" into the floor cavity 43 to below floor level.

The above described embodiment has been given by way of example only, and the skilled reader will naturally appreciate that many variations could be made thereto without departing from the scope of the claims. For example, it is envisaged that the present invention can comprise any suitable movement mechanisms to allow the patient support system to be raised from and lowered into the floor cavity.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the present invention, and exclusive use of all modifications that come within the scope of the appended claims is reserved. It is intended that the present invention be limited only to the extent required by the appended claims and the applicable rules of law.

It is also to be understood that the following claims are to cover all generic and specific features of the invention described herein, and all statements of the scope of the invention which, as a matter of language, might be said to fall therebetween.

What is claimed is:

1. A patient support system, comprising:
   a floor cavity in a floor of a treatment room;
   a patient support device comprising a treatment table;
   a base;
   a first movement mechanism on which the treatment table is mounted; and
   a second movement mechanism mounted on the base and attached to the first movement mechanism;
   wherein the first and second movement mechanisms are moveable independently of each other;
   wherein the first movement mechanism is configured to raise and lower the treatment table and the second movement mechanism is configured to raise and lower the first movement mechanism such that in a lowered position the second movement mechanism is contained within the floor cavity; and
   further comprising a moveable false floor, wherein the false floor is moveable across at least part of an opening of floor cavity.

2. The patient support system of claim 1, wherein when the treatment table is in a lowered position both the first and the second movement mechanisms are contained within the floor cavity.

3. The patient support system of claim 1, wherein the treatment table is configured to extend no more than about 700 mm above a rim of the floor cavity in a towered position.

4. The patient support system of claim 1, wherein the treatment table is configured to extend about 450 mm above a rim of the floor cavity in a lowered position.

5. The patient support system of claim 1, wherein the false floor is hydraulically-powered.

6. The patient support system of claim 1, wherein the false floor is pneumatically-powered.

7. The patient support system of claim 1, wherein the false floor is resiliently biased.

8. The patient support system of claim 1, wherein the false floor is slideable in a direction co-planar with the floor of the treatment room.

9. The patient support system of claim 1, wherein the floor cavity is rectangular with a depth of about 220 to 235 mm, a length of about 1530 mm and a width of about 1400 mm.

10. The patient support system of claim 1, wherein the floor cavity is rectangular with a depth of about 220 to 235 mm, a length of about 530 to 1030 mm and a width of about 140 mm, wherein the width of the floor cavity narrows to a width of about 600 mm.

11. A patient support device, comprising:
    a treatment table;
    a base;
    a first movement mechanism on which the treatment table is mounted; and a second movement mechanism mounted on the base and attached to the first movement mechanism;

wherein the first and second movement mechanisms are moveable independently of each other, wherein the first movement mechanism is configured to adjust a height of the treatment table and the second movement mechanism is configured to adjust the height of the first movement mechanism; and further comprising a moveable false floor, wherein the false floor is moveable across at least part of an opening of a floor cavity.

12. The patient support device of claim 11, wherein when the treatment table is in a lowered position the first and the second movement mechanisms are contained within a floor cavity of a treatment room within which the device is located.

13. The patient support device of claim 11, wherein the treatment table is configured to extend no more than about 700 mm above a rim of a floor cavity in a lowered position.

14. The patient support device of claim 11, wherein the treatment table is configured to extend about 450 mm above a rim of a floor cavity in a lowered position.

15. The patient support device of claim 11, wherein the false floor is hydraulically-powered.

16. The patient support device of claim 11, wherein the false floor is pneumatically-powered.

17. The patient support device of claim 11, wherein the false floor is resiliently biased.

18. The patient support device of claim 11, wherein the false floor is slideable in a direction co-planar with a floor of a treatment room within which the device is located.

* * * * *